Figure 1:
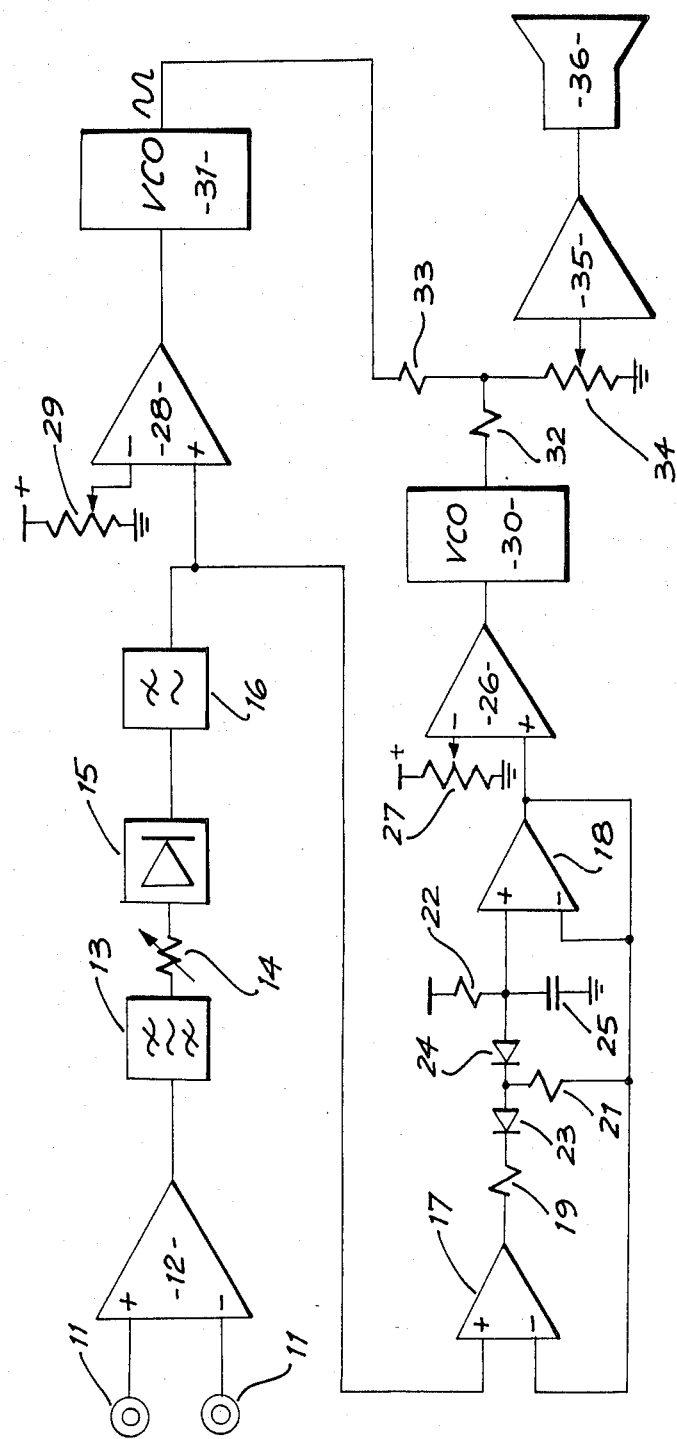

United States Patent [19]

Brown

[11] Patent Number: 4,807,642

[45] Date of Patent: Feb. 28, 1989

[54] ELECTROMYOGRAPHIC REPETITIVE STRAIN INJURY MONITOR

[76] Inventor: David A. Brown, 12 Pritchard Street, Annandale, Australia, 2038

[21] Appl. No.: 56,479

[22] PCT Filed: Aug. 18, 1986

[86] PCT No.: PCT/AU86/00236

§ 371 Date: Apr. 10, 1987

§ 102(e) Date: Apr. 10, 1987

[87] PCT Pub. No.: WO87/01123

PCT Pub. Date: Feb. 26, 1987

[30] Foreign Application Priority Data

Aug. 16, 1985 [AU] Australia ............................ PH01987

[51] Int. Cl.⁴ ................................................ A61B 5/04
[52] U.S. Cl. .................................... 128/733; 307/359
[58] Field of Search ................ 128/733, 905; 307/351, 307/359; 328/151

[56] References Cited

U.S. PATENT DOCUMENTS

| | | | |
|---|---|---|---|
| 3,641,993 | 2/1972 | Gaarder et al. | 128/733 |
| 3,699,357 | 10/1972 | Lloyd | 328/151 |
| 3,743,950 | 7/1973 | Sellari et al. | 328/151 |
| 3,893,180 | 7/1975 | Braun et al. | 307/351 |
| 3,942,516 | 3/1976 | Glynn et al. | 128/733 |
| 4,110,918 | 9/1978 | James et al. | 128/905 |
| 4,170,225 | 10/1979 | Criglar et al. | 128/733 |
| 4,373,140 | 2/1983 | Chin | 307/359 |
| 4,376,266 | 3/1983 | Raffoux | 307/359 |
| 4,433,254 | 2/1984 | Katakura et al. | 307/359 |

FOREIGN PATENT DOCUMENTS 74407 3/1983 European Pat. Off. .
1296996 11/1972 United Kingdom .
2145228 3/1985 United Kingdom .

OTHER PUBLICATIONS

Applied Ergonomics, vol. 16, No. 1, pp. 49–54, Mar. 1985, Granstrom et al, "Electromyography as an Aid in the Prevention of Excessive Shoulder Strain".
European Journal of Applied Physiology and Occupational Physiology, vol. 40, 1979, pp. 265–272, Hagberg, "The Amplitude Distribution of Surface EMG in Static and Intermittent Satic Muscular Performance".

Primary Examiner—Edward M. Coven
Assistant Examiner—John P. Lacyk
Attorney, Agent, or Firm—Nixon & Vanderhye

[57] ABSTRACT

A monitoring device for detecting muscle strain, which might lead to repetitive strain injury includes EMG sensors which generate an EMG signal, signal processing circuitry to derive a signal or signals representative of undesirable strain conditions and an acoustic signal generator which produces a signal to indicate when undesirable strain conditions exist. The signal processor includes a band pass filter to band limit the EMG signal, a rectifier and low pass filter to produce an envelope signal and a minimum signal level tracking circuit comprising amplifiers, capacitor, diodes and resistors. The minimum signal level tracking circuit produces a minimum level signal which tracks the envelope signal, with a short time constant while the minimum level signal is greater than the envelope signal, and with a long time constant when the minimum level signal is less than the envelope signal. The acoustic signal generator produces an acoustic alarm signal when the minimum level signal exceeds a preset threshold level.

11 Claims, 2 Drawing Sheets

ELECTROMYOGRAPHIC REPETITIVE STRAIN INJURY MONITOR

The present invention relates generally to devices for monitoring muscle tension and in particular the invention provides an improved device suitable for use in a work environment to monitor muscle tension of persons performing repetitive tasks and to provide a form of biofeedback, when training operators to minimize muscle tension while performing their allotted tasks.

Musculoskeletal pain in the workpiece (also called "Repetition Strain Injury", "RSI", or "Tenosinovitus" etc.) is currently a significant economic and social problem. Current opinion implicates the sustained low levels of muscle tension as the principal cause of musculo-skeletal pain, with repeated jerky movements being a secondary but still important cause of discomfort. If this condition is not attended to promptly it can also in some cases develop into a serious incapacity, which may effectively prevent an affected individual from following their chosen career.

For many years the method of electromyography (EMG) has been used to monitor muscle tension in the workplace and the information gathered by such measurements has been used to assess procedures in the workplace as well as the design of equipment used, and has proved to be of great value. However, a relatively unexplored use is as a method of training individuals to improve their workstyle. This involves the use of EMG equipment for "biofeedback", where the worker is given information about their muscle activity as they work in order that they may have the opportunity of trying different work methods and to determine quickly which of these methods produces the lowest muscle tension.

A small amount of work has been done in the area of work style biofeedback, both in Australia and overseas, however, a fundamental problem has existed to date in that the equipment used provides the person being trained with a large amount of irrelevant information, making their task of learning much more difficult. This situation has arisen largely because of the way in which the EMG signal is processed and presented to the user, the commonly used method of feedback being unsuitable for this particular purpose.

The EMG waveform is a rapidly fluctuating bipolar signal with an amplitude in the range of 1 to 1000 microvolts and a frequency in the range of several Hz to approximately 1 KHz. The signal in this application is picked up by adhesive surface electrodes placed on the skin covering the muscle whose activity is to be assessed and the signal produced by these electrodes is amplified and is also usually frequency limited to reject interference. The amplified signal is then rectified and passed through a low pass filter to extract the slowly varying (1 Hz or less) envelope of the wave form. It is this slowly varying wave form which has been shown to correlate highly with variations in muscle tension, and which is therefore used for workstation assessment and as the basis of biofeedback training. Most biofeedback EMG instruments process this signal further by comparing it to an adjustable threshold and displaying the difference on a meter or light bar display and may optionally also provide an audible tone whose frequency varies with the relative amplitude of the EMG signal. Usually when the EMG signal is smaller than the threshold level, no sound is heard, enabling the biofeedback device to be used as a "tension alarm", thus alerting the person being trained when their muscle activity exceeds a preset level. This type of signal is certainly of benefit in the case of muscles whose tension rises only when the person becomes too tense, such as with a person who is being trained to perform deep muscle relaxation in a clinic where they are not actually doing anything or performing a simulated work activity. However, real work involves occasional large movements which upset the operation of these simple EMG devices, such that if a typist reaches for a new sheet of paper, for example, the shoulder muscle tension will rise sharply, and the ordinary biofeedback instrument will produce a near maximum sound, whereas these occasional large movements pose no injury risk if they do not exceed some 50% of maximum muscle strength. That is, the instrument gives its maximum response to an event when it should entirely ignore.

The present invention relates to an exemplary EMG monitoring device having signal conditioning means, including rectifier and low pass filter means to produce a signal which is the envelope of an EMG signal being monitored, the filter means having a time constant on the order of 0.1 seconds, minimum signal detection means to produce a minimum level signal which tracks the minimum peaks of said envelope signal, the minimum level detection circuit including a low pass filter with a first time constant in the range of 1-2 seconds and rate limiting circuit to limit the rate of change of the output of the minimum level detection circuit in response to an increasing EMG envelope signal, the rate limiting circuit having a time constant in the range of 5 seconds to 10 minutes such that the minimum level signal produced by said minimum signal detection means has a fast attack to the minimum value of the EMG envelope signal and a slow decay to the maximum value of the EMG envelope signal, and indicating means to indicate the difference between the minimum level signal and a predetermined threshold value.

In a preferred embodiment, the indicating means comprises variable frequency tone generating means responsive to the minimum level signal to produce an audio frequency signal the frequency of which is proportional to the difference between said minimum signal and a predetermined threshold value, and transducer means for converting said audio frequency signal into an acoustic tone.

The preferred embodiment of the invention also provides a maximum signal detector, to detect peaks in said envelope signal, and a second audio frequency signal generator, to generate a high pitch audio tone when the output of the maximum signal detector exceeds a predetermined threshold value, the output of the first and second audio frequency tone generators being mixed in a mixer before being amplified and fed to the transducer which produces the acoustic tone.

Figure 2A:
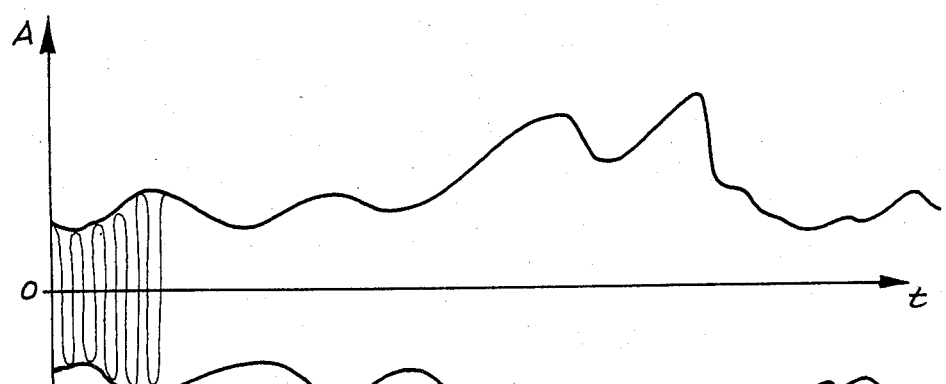
Figure 2B:
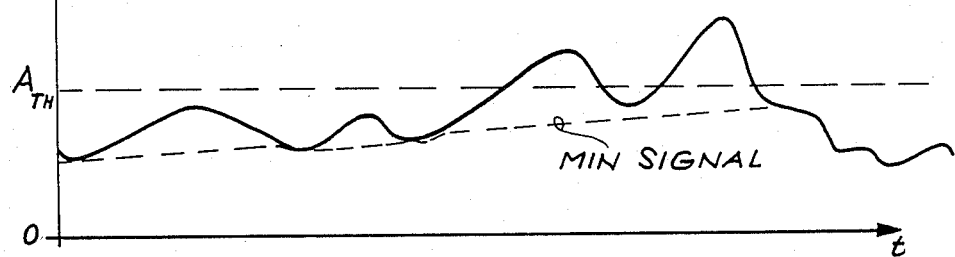
Figure 2C:
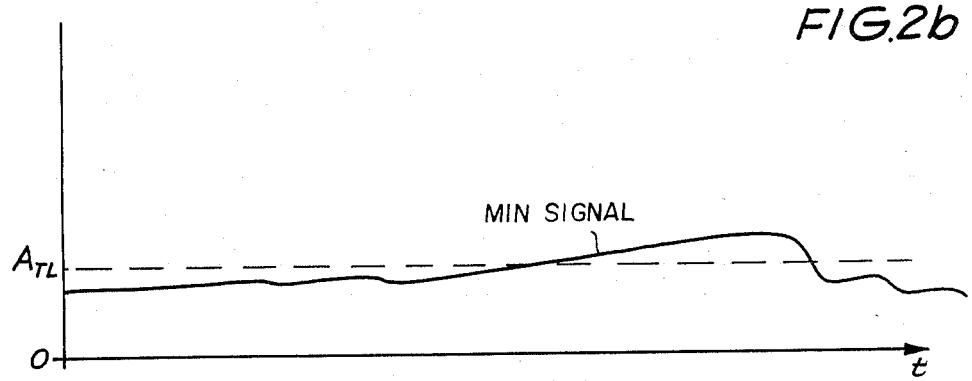

An embodiment of the invention will now be described, by way of example, with reference to the accompanying drawings in which:

FIG. 1 schematically illustrates the circuit of an embodiment of the present invention; and FIG. 2 graphically illustrates (a) a bipolar EMG signal, (b) an envelope signal derived from the signal of FIG. 2(a), and (c) a minimum signal derived from the envelope signal of FIG. 2(b).

Referring to FIG. 1, EMG signals are detected using adhesive surface electrodes 11 placed on the skin covering the muscle whose activity is to be assessed. The EMG signal produced by electrodes 11 is then amplified in amplifier 12 before being passed through a band pass filter 13 having a pass band in the range 100 to 200 Hz. Amplifier 12 is a differential instrumentation amplifier having a common mode rejection ratio (CMRR) of greater than 70 dB and a gain in the range of 100 to 1000. The output of the band pass filter 13 is passed through a gain adjusting potentiometer 14 before being rectified by rectifier 15 and passed through a low pass filter 16, having a time constant $\tau$ in the order of 0.1 seconds, to produce the envelope of the EMG signal (see (FIG. 2(b), solid line).

The envelope of the EMG signal produced by filter 16 is then fed to a minimum signal detector circuit comprising amplifiers 17 and 18, resistors 19, 21 and 22, diodes 23 and 24 and capacitor 25. The minimum signal detector circuit provides a slow decay to peak value $V_c$ and a fast attack to minimum value of the EMG signal (e.g., when the EMG signal itself falls below the output of the detector circuit amplifier 18). The different attack and decay time constants are produced by virtue of diodes 23 and 24 which essentially cause the capacitor 25 to track the output of filter 16 when the output of amplifier 18 is greater than or equal to the envelope signal out of filter 16 and to slowly charge towards the control voltage $V_c$ via resistor 22 when the output of amplifier 18 is less than the output of filter 16. The control voltage $V_c$ can either be a predetermined fixed value, such as is provided by the positive supply rail or alternatively it may be a time varying signal derived from the EMG signal.

The output of the minimum signal detection circuit, generated by amplifier 18, is passed to a threshold detection circuit 26 which compares the minimum value signal with a reference signal generated by a potentiometer 27. The output of the threshold detection circuit is proportional to the difference between the voltage generated by the potentiometer 27 and the voltage out of amplifier 18 when that difference is negative and is zero at other times. This signal is used to vary the frequency of a voltage controlled oscillator (VCO) 30, such that when the output from the threshold detection circuit 26 is zero the VCO 30 does not produce an output and as the output of the threshold detection circuit 26 increases the VCO commences to oscillate at a low frequency, the frequency of oscillation gradually increasing with increasing minimum muscle tension value.

As mentioned above, the control voltage $V_c$ may be made to be time varying, and in the preferred embodiment, this signal would be derived as a function of the envelope of the rectified EMG signal.

In embodiments where the control voltage $V_c$ is fixed, the decay time is dependent on only the difference between the initial EMG level and the threshold voltage. On the other hand, where the control voltage $V_c$ is a function of the rectified EMG signal, then the decay time will be shorter when the EMG signal is larger, and longer when it is lower. The benefit of this arrangement is that, for a given time constant, a longer period of work between micropauses will be allowed without causing the VCO 30 to oscillate, when a relatively relaxed workstyle is being used, but the allowed period will be shortened when a tense workstyle is being used.

The envelope signal generated by filter 16 is also fed to a second threshold detection circuit 28 which compares the envelope signal with an upper threshold generated by a potentiometer 29 and produces an output when the envelope exceeds this threshold value. The output of the threshold detector 28 is also fed to a second VCO 31 which commences oscillating at a frequency significantly higher than that of VCO 30, when a positive output is detected from the threshold detector circuit 28.

The outputs of VCO 30 and VCO 31 are mixed by resistors 32 and 33 before passing through a gain adjusting potentiometer 34 to an output amplifier 35 which drives a speaker 36 to produce audible tones.

In operation, the VCO's 30 and 31 do not produce an output until such time as either the minimum tension value climbs above a preset level determined by the potentiometer 27, in which case the VCO 30 will commence to produce a low frequency tone which increases in frequency as the tension increases above the preset level, or alternatively until the peak value of the tension signal increases above a second preset level determined by potentiometer 29 in which case a higher frequency tone is generated by VCO 31. In effect, this means that the monitor is detecting two different situations, the first being a minimum stress level which remains above the preset level determined by potentiometer 27 for a period longer than that set by the time constant of resistor 22 and capacitor 25, while the second condition is an absolute peak tension level which exceeds a threshold set by potentiometer 29.

Referring to FIG. 2(a), a portion of a bipolar EMG signal typical of the output of amplifier 12 is graphically illustrated, while in FIG. 2(b) the positive envelope of this signal, generated at the output of filter 16 is illustrated. In FIG. 2(b) a typical upper threshold $A_{th}$, as would be set by potentiometer 29, is also illustrated. In the circuit of FIG. 1 the signal generated by VCO 31 will be present at the output of the monitor during those periods where the envelope signal of FIG. 2(b) exceeds the threshold $A_{th}$. A second dotted line is also illustrated in FIG. 2(b) and is designated MIN SIGNAL, this being the signal generated at the output of amplifier 18. The MIN SIGNAL of FIG. 2(b) is illustrated separately in FIG. 2(c) together with a lower threshold level $A_{tl}$ and it will be seen that this minimum value signal tracks the envelope signal closely when the envelope signal is descending but ramps at a substantially constant rate of increase e.g., towards an upper limit $V_c$ which may be fixed or which may vary with the EMG signal) when the envelope signal increases. The rate of ramping of the minimum value signal is determined by the time constant of the RC circuit formed by resistor 22 and capacitor 25 while the rate at which the minimum value signal can follow the envelope signal when it is decreasing in value is determined by the time constant provided by resistor 19 and capacitor 25. In practice the value of resistor 19 will be significantly smaller than the value of resistor 22 and the time constant of minimum value signal is selected to be in the range of 1 to 2 seconds such that the minimum value signal will closely track descending portions of the envelope signal. On the other hand, the time constant determined by resistor 22 and capacitor 25 is typically selected to be in the range of 5 seconds to 10 minutes depending upon the application. It has been shown that the minimum time required for blood to move through a muscle and so refresh the muscle tissues is 1 to 2 seconds, this being the determining factor for selecting the discharge time constant for capacitor 25. The charge time constant of capacitor 25 is set at a convenient value for the task at hand, for example typing tasks require a pause in tension every 1-5 minutes and hence when using the device as a tension alarm a time constant in this range would be selected, while when training typists to improve their style a time constant in the range of 5-30 seconds is preferable to provide continuous biofeedback. The effect of this assymetric time constant is that the person being trained will not be interrupted if their muscle tension exceeds criterion unless it has been doing so for some time, which is dependent on the length of their short relaxation pauses and on the degree to which they have been exceeding the criterion level of muscle activity. Therefore the schedule of work/pause can be set according to what is known about optimum work/pause cycles.

The circuit of FIG. 1 also provides a response which correctly applies known learning principles. Learning requires that the activity, in this case relaxing, should be followed as soon as possible with the reinforcement, in this case cessation of the tone. By choosing a time constant for the discharge, or relaxation measuring phase of the signal, such that a quick response is obtained, the requirements of effective learning are met as well as those for correct muscle use.

The requirements for measuring peak load are quite different. Peak loads are a potential problem when they exceed 50-60% of maximum strength in a muscle, on a frequent basis. The biofeedback signal must recognize peak loads lasting as little as 0.1 seconds, which is too short an interval for most biofeedback instruments whereas the high level peak detection circuit 28 of FIG. 1 performs this function.

The instrument of FIG. 1 is unique in that it measures the static load component of the electromyogram, thereby identifying the principal cause of discomfort. Although the measurement of static load has been previously accomplished in European research efforts, there has never been a portable instrument which analyses this and provides the result to the person being trained so as to inform them of their own injury risk. Previous applications have not included a training (biofeedback) component, but have concentrated exclusively on technical assessment. The present device takes this concept of static load and measures it in a much more simple way than previous methods, and in addition provides the needed feedback signal which is based on both physiological principles of latency of blood flow, and on learning principles of the optimum conditions for learning of new activities.

In addition to providing feedback on the static load component, the preferred embodiment also provides feedback about momentary excessive peak loads. This is done by providing a second audible signal at a higher frequency than the first, and a list of output signals for given muscle conditions is given below.

| Condition | Audible signal |
| --- | --- |
| Tension below threshold | No signal |
| Tension above static load threshold | Signal appears after preset time. Low frequency sound increasing slowly in pitch, terminated immediately following relaxation of the excessive tension |
| Tension suddenly peaks, but not above peak load threshold | No audible sound |
| Tension rises above peak load threshold | Immediate sound. High pitch |
| Both excessive static and peak loads | Both low and high pitch tones sound together |

It will be recognised by persons skilled in the art that numerous variations and modifications may be made to the invention as described above without departing from the spirit or scope of the invention as broadly described.

I claim:

1. An EMG monitoring device comprising:

signal conditioning means, including rectifier and low pass filter means to produce a signal which is the envelope of an EMG signal being monitored, said filter means having a time constant on the order of 0.1 seconds, minimum signal detection means to produce a minimum level signal which tracks the minimum peaks of said envelope signal, minimum signal detection means including a low pass filter with a first time constant in the range of 1-2 seconds and rate limiting circuit means to limit the rate of change of the output of the minimum signal detection means in response to an increasing EMG envelope signal, the rate limiting circuit means having a time constant in the range of 5 seconds to 10 minutes such that the minimum level signal produced by said minimum signal detection means has a fast attack to the minimum value of the EMG envelope signal and a slow decay to the maximum value of the EMG envelope signal, and indicating means to indicate the difference between the minimum level signal and a predetermined threshold value.

2. The monitoring device of claim 1 wherein the rate limiting circuit means of the minimum signal detection means comprises:

a capacitor which is charged through a resistor, and means to define the upper limit of the charge on the capacitor such that the upper limit of the charge is substantially determined by the instantaneous value of the envelope of the EMG signal and wherein a charging voltage applied to the resistor is a function of said envelope of the EMG signal.

3. The monitoring device of claim 1 wherein the rate limiting circuit means of the minimum signal detection means comprises:

a capacitor which is charged through a resistor, and means to define the upper limit of the charge on the capacitor such that the upper limit of the charge is substantially determined by the instantaneous value of the envelope of the EMG signal and wherein a charging voltage applied to the resistor is a fixed reference voltage.

4. The monitoring device of claim 1 wherein the indicating means includes:

a variable first frequency signal generating means, responsive to the minimum level signal to produce an audio frequency signal, the frequency of which is proportional to the difference between said minimum signal and a predetermined threshold value, and transducer means for converting said audio frequency signal to an audible tone.

5. The monitoring device of claim 3 wherein the indicating means includes:

a variable first frequency signal generating means, responsive to the minimum level signal to produce an audio frequency signal, the frequency of which is proportional to the difference between said minimum signal and a predetermined threshold value, and transducer means for converting said audio frequency signal to an audible tone.

6. The monitoring device as claimed in claim 4, wherein a maximum signal detector is provided comprising:

a comparator means to compare the envelope signal with a predetermined maximum threshold value and to produce an output which indicates when the envelope signal exceeds said maximum threshold, and second audio frequency generating means responsive to the comparator means output signal to produce a high frequency audio signal which is fed to said transducer means.

7. The monitoring device as claimed in claim 6 further comprising signal mixing means and wherein the output of first and second generating means are mixed in said mixing means before being fed to the transducer means which produces acoustic tones.

8. The monitor device as claimed in claim 6 or 7 wherein the maximum signal detector includes means that detects peak signals having a minimum duration of on the order of 0.1 seconds.

9. The monitoring device as claimed in claim 1, 2, 3, 4, 5, 6 or 7 wherein the rate limiting circuit means of the minimum signal detection means has a time constant in the range of 5-30 seconds.

10. The monitoring device as claimed in claim 1, 2, 3, 4, 5, 6 or 7 wherein the rate limiting circuit means of the minimum signal detection means has a time constant in the range of 1-5 minutes.

11. An EMG monitoring device comprising:

first signal processing means for accepting an input EMG signal and for producing an EMG envelope signal representing the envelope of a filtered version of the input EMG signal;

second signal processing means for accepting said envelope signal and for producing an output signal which (a) increases toward an upper limit with a first time lag and (b) decreases with a second time lag to closely follow said envelope signal when it is less than said output signal, said second time lag being substantially less than said first time lag; and indicator means for producing a humanly sensible stimulus in response to excessive excursions of said output signal.

* * * * *